United States Patent
Nagae (10) Patent No.: US 10,937,136 B2
(45) Date of Patent: Mar. 2, 2021

(54) SUBJECT INFORMATION PROCESSING APPARATUS AND IMAGE DISPLAY METHOD

(71) Applicant: CANON KABUSHIKI KAISHA, Tokyo (JP)

(72) Inventor: Kenichi Nagae, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/859,105

(22) Filed: Dec. 29, 2017

(65) Prior Publication Data

US 2018/0197283 A1 Jul. 12, 2018

(30) Foreign Application Priority Data

Jan. 6, 2017 (JP) .............................. JP2017-001409

(51) Int. Cl.
*G06T 5/50* (2006.01)
*G06T 7/246* (2017.01)
(Continued)

(52) U.S. Cl.
CPC .............. *G06T 5/50* (2013.01); *A61B 5/0095* (2013.01); *A61B 5/7425* (2013.01); *G01N 29/22* (2013.01);
(Continued)

(58) Field of Classification Search
None
See application file for complete search history.

(56) References Cited

U.S. PATENT DOCUMENTS

2004/0174385 A1* 9/2004 Ikeda ..................... G09G 5/393
345/629
2006/0125804 A1* 6/2006 Kent ..................... G06F 3/0436
345/177
(Continued)

FOREIGN PATENT DOCUMENTS

CN 101547308 A 9/2009
CN 102446352 A 5/2012
(Continued)

OTHER PUBLICATIONS

Thomas Chaigne, Jérôme Gateau, Marc Allain, Ori Katz, Sylvain Gigan, Anne Sentenac, and Emmanuel Bossy, "Super-resolution photoacoustic fluctuation imaging with multiple speckle illumination," Optica 3, 54-57 (2016).*
(Continued)

*Primary Examiner* — Jiangeng Sun
(74) *Attorney, Agent, or Firm* — Canon U.S.A., Inc. I.P. Division (57) ABSTRACT

There are provided a subject information processing apparatus suitable for acquiring a moving image by consecutively receiving acoustic waves from an observation target subject region and an image display method. First combined image data is generated by combining at least two of i-th image data to (i+m)-th image data (i+m<N, where i and m are natural numbers) out of N pieces of image data based on electrical signals acquired when a probe detects the acoustic waves respectively at N positions (N is 3 or a larger integer) at different relative positions to the subject. Second combined image data is generated by combining at least two of an (i+n)-th to an (i+n+m)-th image data (n is a natural number). An image based on the first combined image data is updated to an image based on the second combined image data.

16 Claims, 6 Drawing Sheets

(51) Int. Cl.
*G06T 1/00* (2006.01)
*G01N 29/22* (2006.01)
*A61B 5/00* (2006.01)

(52) U.S. Cl.
CPC ............ *G06T 1/0007* (2013.01); *G06T 7/246* (2017.01); *A61B 5/743* (2013.01); *A61B 2576/00* (2013.01); *G06T 2207/10132* (2013.01); *G06T 2207/20212* (2013.01)

(56) References Cited

U.S. PATENT DOCUMENTS

| | | | |
|---|---|---|---|
| 2014/0221836 A1* | 8/2014 | Takeda | A61B 8/463 600/443 |
| 2015/0065881 A1* | 3/2015 | Cho | A61B 8/54 600/443 |
| 2016/0100821 A1* | 4/2016 | Eggers | A61B 8/4254 600/424 |
| 2016/0135688 A1 | 5/2016 | Ebisawa | |
| 2016/0150990 A1 | 6/2016 | Ohkoba | |

FOREIGN PATENT DOCUMENTS

| | | | |
|---|---|---|---|
| CN | 105472204 A | 4/2016 | |
| CN | 105640496 A | 6/2016 | |
| CN | 105979878 A | 9/2016 | |
| JP | H08-336530 A | 12/1996 | |
| JP | 2006041744 A | 2/2006 | |
| JP | 2009172030 A | 8/2009 | |
| JP | 2012-196308 A | 10/2012 | |
| JP | 2014140716 A | 8/2014 | |
| JP | 201647102 A | 4/2016 | |
| JP | 2016209173 A | 12/2016 | |
| WO | WO-2007018338 A1 * | 2/2007 | ......... G01S 7/52092 |
| WO | 2013134772 A2 | 9/2013 | |
| WO | 2015174085 A1 | 11/2015 | |
| WO | WO-2015174085 A1 * | 11/2015 | ........... A61B 5/0095 |

OTHER PUBLICATIONS

Jérôme Gateau, Thomas Chaigne, Ori Katz, Sylvain Gigan, and Emmanuel Bossy, "Improving visibility in photoacoustic imaging using dynamic speckle illumination," Opt. Lett. 38, 5188-5191 (2013).*

* cited by examiner

SUBJECT INFORMATION PROCESSING APPARATUS AND IMAGE DISPLAY METHOD

BACKGROUND

Technical Field

The present invention relates to a subject information processing apparatus and an image display method.

Description of the Related Art

There is known a subject information processing apparatus that acquires intra-subject characteristic information by detecting photoacoustic waves generated when a subject is irradiated with light. Japanese Patent Application Laid-Open No. 2016-47102 discusses a photoacoustic imaging apparatus that irradiates a subject with light and acquires photoacoustic wave detection signals at sampling cycles shorter than image refresh cycles. The apparatus discussed in Japanese Patent Application Laid-Open No. 2016-47102 displays a moving image by generating images by averaging the detection signals.

SUMMARY

An apparatus discussed in Japanese Patent Application Laid-Open No. 2016-47102 is considered to acquire a moving image in a state where the relative position of a probe for acquiring a photoacoustic wave to a subject remains unchanged. If photoacoustic waves are repetitively acquired in a state where the relative position of the probe to the subject remains unchanged, random noise contained in the detection signals can be reduced by averaging the detection signals. However, artifacts occurring during reconstruction are not reduced.

In view of an above-described problem, the present invention is directed to a subject information processing apparatus for acquiring a moving image by consecutively receiving acoustic waves from an observation target subject region, and an image display method.

According to an aspect of the present invention, a subject information processing apparatus includes a signal processing unit configured to generate image data of a subject based on electrical signals output from a probe detecting acoustic waves propagated from the subject, and a display control unit configured to control a display unit to display an image based on the image data. The signal processing unit combines at least two of i-th image data to (i+m)-th image data (i+m<N, where i and m are natural numbers) out of N pieces of image data based on electrical signals acquired when a probe detects the acoustic waves respectively at N positions (N is 3 or a larger integer) at different relative positions to the subject to generate first combined image data. The signal processing unit combines at least two of (i+n)-th image data to (i+n+m)-th image data (n is a natural number) to generate second combined image. The display control unit controls the display unit to display an image based on the first combined image data, and further updates the image displayed on the display unit to an image based on the second combined image data.

According to another aspect of the present invention, a subject information processing apparatus includes a signal processing unit configured to generate image data of a subject based on electrical signals output from a probe detecting acoustic waves propagated from the subject, and a display control unit configured to control a display unit to display an image based on the image data. The signal processing unit uses at least two of an i-th to an (i+m)-th electrical signal (i+m<N, where i and m are natural numbers) out of N electrical signal groups acquired when a probe detects the acoustic waves respectively at N positions (N is 3 or a larger integer) at different relative positions to the subject to generate first combined image data. The signal processing unit uses at least two of an (i+n)-th to an (i+n+m)-th electrical signal (n is a natural number) to generate second combined image. The display control unit controls the display unit to display an image based on the first combined image data, and further updates the image displayed on the display unit to an image based on the second combined image data.

Further features of the present invention will become apparent from the following description of exemplary embodiments with reference to the attached drawings.

DESCRIPTION OF THE EMBODIMENTS

Exemplary embodiments of the present invention will be described in detail below with reference to the accompanying drawings. Basically, identical elements are assigned the same reference numerals and redundant descriptions thereof will be omitted. Note that, detailed calculation formulas and calculation procedures described below are not limited thereto, and should be modified as required depending on the configuration of an apparatus to which the present invention is applied and other various conditions. The scope of the present invention is not limited to the following descriptions.

A subject information processing apparatus according to an exemplary embodiment of the present invention includes an apparatus utilizing a photoacoustic effect. More specifically, the apparatus irradiates a subject (for example, breast, face, or palm) with light (electromagnetic wave) such as near-infrared ray, receives an acoustic wave generated in the subject, and acquires subject information as image data.

In a case of an apparatus utilizing a photoacoustic effect, the acquired subject information indicates a generation source distribution of acoustic waves generated by light irradiation, an intra-subject initial sound pressure distribution or an optical energy absorption density distribution or an absorption coefficient distribution derived from the initial sound pressure distribution, and a tissue constituent concentration distribution. The constituent concentration distribution is, for example, an oxygen saturation distribution, a total hemoglobin concentration distribution, or an oxidization/reduction hemoglobin concentration distribution.

The characteristic information constituting the subject information at a plurality of positions may be acquired as a two-dimensional or three-dimensional characteristic distribution. A characteristic distribution may be generated as image data indicating intra-subject characteristic information. An acoustic wave according to the present invention typically refers to an ultrasonic wave, and includes an elastic wave called a sound wave or an ultrasonic wave. The acoustic wave generated by the photoacoustic effect is referred to as a photoacoustic wave or a photoacoustic ultrasonic wave. An acoustic wave detector (for example, a probe) receives an acoustic wave generated in the subject.

Figure 1:
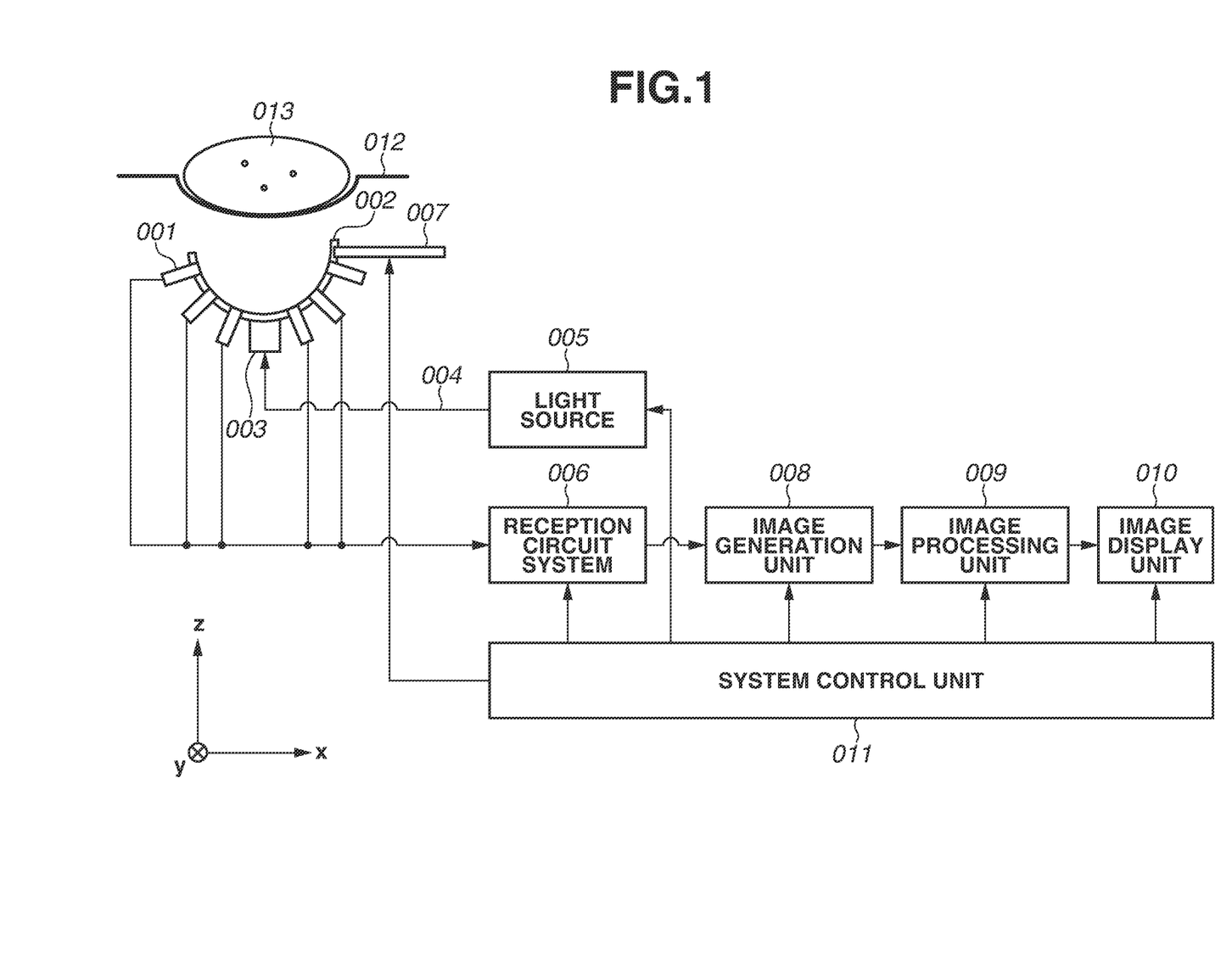
FIG. 1 is a block diagram illustrating a configuration of a subject information processing apparatus according to an exemplary embodiment of the present invention.

FIG. 1 is a block diagram illustrating a subject information processing apparatus according to a first exemplary embodiment of the present invention. The subject information processing apparatus according to the first exemplary embodiment includes a supporting member 002 having a plurality of acoustic wave detection elements 001, an irradiation optical system 003, a transmission system 004, a light source 005, a reception circuit system 006, a sensor array moving mechanism 007, an image generation unit 008, an image processing unit 009, an image display unit 010, a system control unit 011, and a subject supporting member 012.

The probe includes the supporting member 002 and a plurality of the acoustic wave detection elements 001 arranged on the supporting member 002. Each of the acoustic wave detection elements 001 detects a photoacoustic wave propagated from a subject 013 and converts the photoacoustic wave into an electrical signal (hereinafter also referred to as a photoacoustic signal). The acoustic wave detection elements 001 may be implemented by using an arbitrary element based on a piezoelectrical effect, an optical resonance, or a capacitance variation. The arbitrary element is not limited thereto, and any type of element is applicable as long as an acoustic wave can be received. According to the present exemplary embodiment, the supporting member 002 has a hemispherical inner surface shape along which acoustic wave detection surfaces of a plurality of the acoustic wave detection elements 001 are arranged. With this arrangement, highest receiving sensitivity directions, i.e., directional axes, are concentrated around the center of the hemisphere. The region where high receiving sensitivity directions of a plurality of the acoustic wave detection elements 001 are concentrated makes it possible to acquire more accurate subject information than other regions. The shape of the supporting member 002 is not limited to a hemisphere, and may be a shape of an arbitrary cross section of an ellipse, a polyhedron, or other configurations in which high receiving sensitivity directions of a plurality of the acoustic wave detection elements 001 are concentrated in a predetermined region. Further, the supporting member 002 may one-dimensionally or two-dimensionally support a plurality of the acoustic wave detection elements 001. Using a probe having a plurality of the acoustic wave detection elements 001 arranged multidimensionally enables simultaneously receiving acoustic waves at a plurality of positions, thus shortening the measurement time.

A high resolution region refers to a region where it is possible to acquire a receiving sensitivity of at least a half of the receiving sensitivity at the position with the highest receiving sensitivity determined by the arrangement of the acoustic wave detection elements 001. In the configuration according to the present exemplary embodiment, the center of the hemispherical supporting member 002 is the position with the highest receiving sensitivity, and the high resolution region refers to a spherical region isotopically extending from the center of the hemisphere.

The light source 005 emits light based on a control signal from the system control unit 011. The light emitted from the light source 005, with the shape of the light deformed by the irradiation optical system 003, irradiates the subject 013. The light generated by the light source 005 may be pulsed light having a pulse width of approximately to 100 ns. This configuration makes it possible to efficiently generate a photoacoustic wave. The light source 005 can be a high power laser capable of transmitting light deep inside the subject 013. However, the light source 005 is not limited thereto and may be a light emitting diode or a flash lamp instead of a laser. Lasers applicable to the light source 005 include a solid-state laser, a gas laser, a dye laser, a semiconductor laser, and other various types of lasers. The wavelength of the light generated by the light source 005 is desirably a wavelength with which the light is propagated deep inside the subject 013. For example, if the subject 013 is a living body, the wavelength may be 500 nm or more and 1200 nm or less. The laser used for the light source 005 may be other laser having high power and a continuously variable wavelength, such as an Nd:YAG excitation Ti:sa laser and an alexandrite laser. The light source 005 may include a plurality of single-wavelength lasers of different wavelengths.

The light emitted from the light source 005 is transmitted to the irradiation optical system 003 serving as a light irradiation unit via the transmission system 004. An optical absorber (a new blood vessel, cancer, etc. if the subject 013 is a living body) in the subject 013 generates a photoacoustic wave by absorbing the energy of the light irradiating the subject 013 as described above. The transmission system 004 may include, for example, a plurality of hollow wave guide tubes connected with each other by joints including a mirror. The transmission system 004 may use a multi-joint arm configured to enable light propagation in these wave guide tubes, or a light guide configured to enable light propagation through space by using optical elements such as mirrors and lenses. In addition, the transmission system 004 may include a bundle fiber.

The reception circuit system 006 performs sampling processing and amplification processing on received signals output from a plurality of the acoustic wave detection elements 001, converts the signals into digital signals, and transmits the digital signals to the image generation unit 008. The reception circuit system 006 includes, for example, a signal amplifier such as an operational amplifier, and an analog/digital converter (ADC).

The image generation unit 008 performs image reconstruction processing by using the digital signals transmitted from the reception circuit system 006. The image reconstruction processing is carried out to calculate, for example, the initial sound pressure distribution p (r) of photoacoustic waves in the subject 13 by using filtered back projection (FBP). The FBP is an image reconstruction method, for example, based on the following formula (1).

$$p(r) = -\frac{1}{2\pi} \int_{S_0} \int \frac{dS_0}{r_0^2} \left[ t \frac{\partial p_d(r_0, t)}{\partial t} + 2 p_d(r_0, t) \right]_{t=|r-r_0|/c} \quad \text{[Formula (1)]}$$

where dS0 represents the size of the detector, S0 represents the opening size used for the reconstruction, pd(r,t) represents a signal received by each acoustic wave detection element, t represents a reception time, and r0 represents the position of each acoustic wave detection element.

An image generation unit 008 transmits reconstruction data generated by performing the above-described image reconstruction processing to the image processing unit 009. The image generation unit 008 may include, for example, a central processing unit (CPU) including a multi-core CPU, a Field Programmable Gate Array (FPGA), a workstation, or hardware.

The image processing unit 009 performs, for example, gain correction processing and noise component suppression (through a Gaussian filter or a median filter) on the reconstruction data generated by the image generation unit 008. Then, the image processing unit 009 generates a maximum intensity projection (MIP) image from a specific direction, generates a projection image with the coloring, saturation, and brightness changed depending on the position in a specific direction and the distance from a specific position or plane, and outputs the generated image as image data. The image processing unit 009 also performs various types of image processing such as emphasis processing on a region specified by an operator, and transmits image display data to the image display unit 010. The image processing unit 009 also functions as a display control unit together with the system control unit 011.

The image display unit 010 having a role of a user interface displays image display data input thereto as a visually recognizable image. The image display unit 010 includes a display unit for displaying an image. The image display unit 010 may be provided with a touch panel to also function as an input unit for receiving an instruction from a user. Alternatively, the image display unit 010 may include the display unit and the input unit as different hardware components.

The above-described components may be implemented by common hardware. For example, the image generation unit 008 and the image processing unit 009 may be integrally configured as a signal processing unit having the functions thereof.

The sensor array moving mechanism 007 as a moving unit moves the probe including the supporting member 002 and the acoustic wave detection elements 001 relatively to the subject 013. The effects of the present invention are obtained if the relative position of the probe to the subject 013 changes. Accordingly, the subject 013 may be moved with the probe position fixed, or both the probe and the subject 013 may be moved to change the relative position of the probe to the subject 013. The sensor array moving mechanism 007 includes a movable stage for moving the supporting member 002 relatively to the subject 013. The sensor array moving mechanism 007 can perform two-dimensional relative movement of the supporting member 002 in the x-y plane and also three-dimensional relative movement thereof in a space including the z direction illustrated in FIG. 1.

Figure 2:
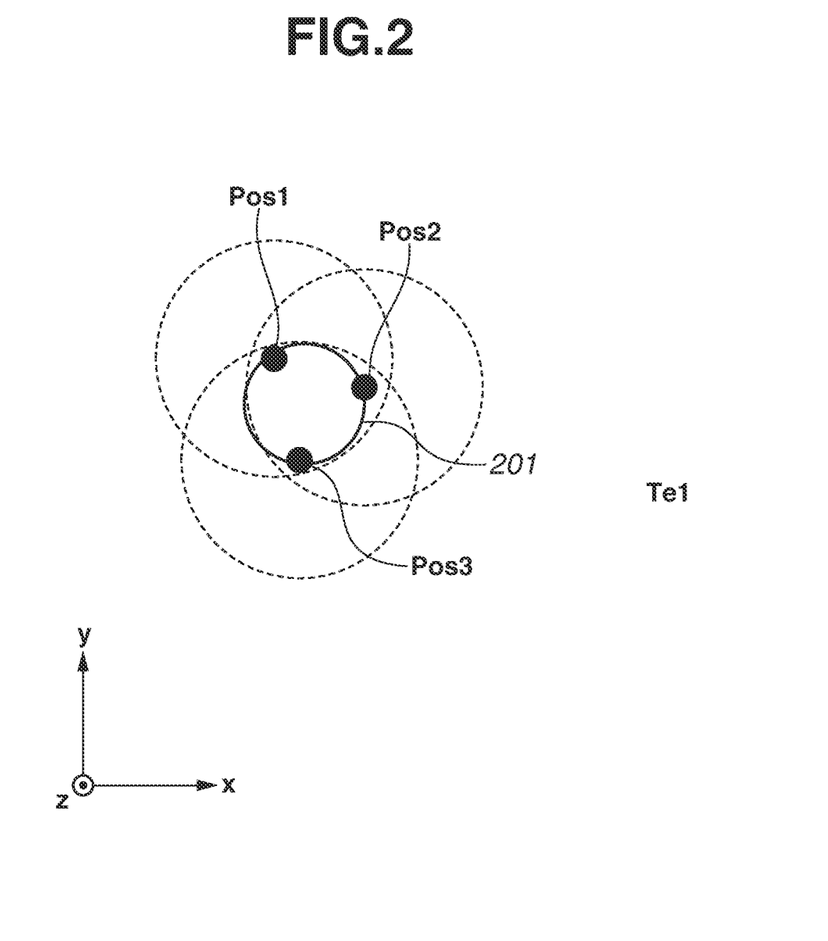
FIG. 2 is a diagram illustrating a movement of a probe according to a first exemplary embodiment.

FIG. 2 schematically illustrates the movement of the supporting member 002 according to the present exemplary embodiment. When the sensor array moving mechanism 007 moves the probe in the x-y plane, the center of the high resolution region of the probe draws a track 201. Referring to FIG. 2, positions Pos1, Pos2, and Pos3 indicate positions of the center of the high resolution region at timings Te1, Te2, and Te3, respectively, when the light irradiation is performed on the subject 013. The circles drawn by dotted lines centering on the positions Pos1, Pos2, and Pos3 schematically illustrate spreading of the high resolution region at respective positions.

In this way, the system control unit 011 performs the light irradiation at a plurality of positions where the high resolution regions overlap, and performs the image reconstruction by using acquired photoacoustic signals. In the high resolution region, since high directivity regions of a number of the acoustic wave detection elements 001 overlap, photoacoustic signals generated from the regions can be acquired with a high signal-to-noise (S/N) ratio. Artifacts on an image acquired through image reconstruction can be reduced by performing the image reconstruction by using photoacoustic signals acquired at different relative positions of the supporting member 002 to the subject 013.

Operations of the image generation unit 008 and the image processing unit 009 will be described below. The image generation unit 008 performs the image reconstruction by using photoacoustic signals output from the reception circuit system 006, and outputs the signals as volume data. The image generation unit 008 separately performs the image reconstruction on the acquired photoacoustic signals for each light irradiation. The image processing unit 009 combines a plurality of photoacoustic volumes to calculate combined volume data with reduced artifacts. Hereinafter, volume data and combined volume data are also referred to as image data and combined image data, respectively. Referring to the example illustrated in FIG. 2, the system control unit 011 performs the light irradiation at a timing when the center of the high resolution region is at the position Pos1. Then, the image generation unit 008 performs the image reconstruction for a space including the high resolution region indicated by a dotted line centering on the position Pos1 by using an acquired photoacoustic signal through the light irradiation, and acquires volume data 1. Then, the system control unit 011 performs the light irradiation at a timing when the center of the high resolution region is at the position Pos2. The image generation unit 008 then performs the image reconstruction for a space including the high resolution region drawn with a dotted line centering on the position Pos2 by using an acquired photoacoustic signal through the light irradiation, and acquires volume data 2. When the center of the high resolution region is at the position Pos3, the image generation unit 008 acquires volume data 3 in a similar way.

The image processing unit 009 combines the above-described three different volume data while maintaining the relative positional relations to calculate combined volume data 1. This makes it possible to acquire photoacoustic images with reduced artifacts in overlapping regions of each piece of volume data. Assume that the high resolution region is a schematically spatially arranged spherical or cylindrical region having a radius R, and that at least two of the positions of the center of the high resolution region at the time of light irradiation have a distance L. It is desirable that a relation L<R is satisfied to obtain the above-described effects.

If the probe movement is controlled so that the high resolution regions overlap regardless of the position of the supporting member 002 on the track 201, it is possible to perform the image reconstruction by using a larger number of photoacoustic signals and further acquire photoacoustic images with reduced artifacts. For example, assuming that the circular track 201 has a radius Rrot, this effect can be obtained by controlling the probe movement based on a relation Rrot<R. Further, if the probe movement is controlled based on a relation Rrot<R/2, the high resolution regions overlap in all regions within 201, making it possible to acquire photoacoustic images with reduced artifacts in a wider range.

Figure 3:
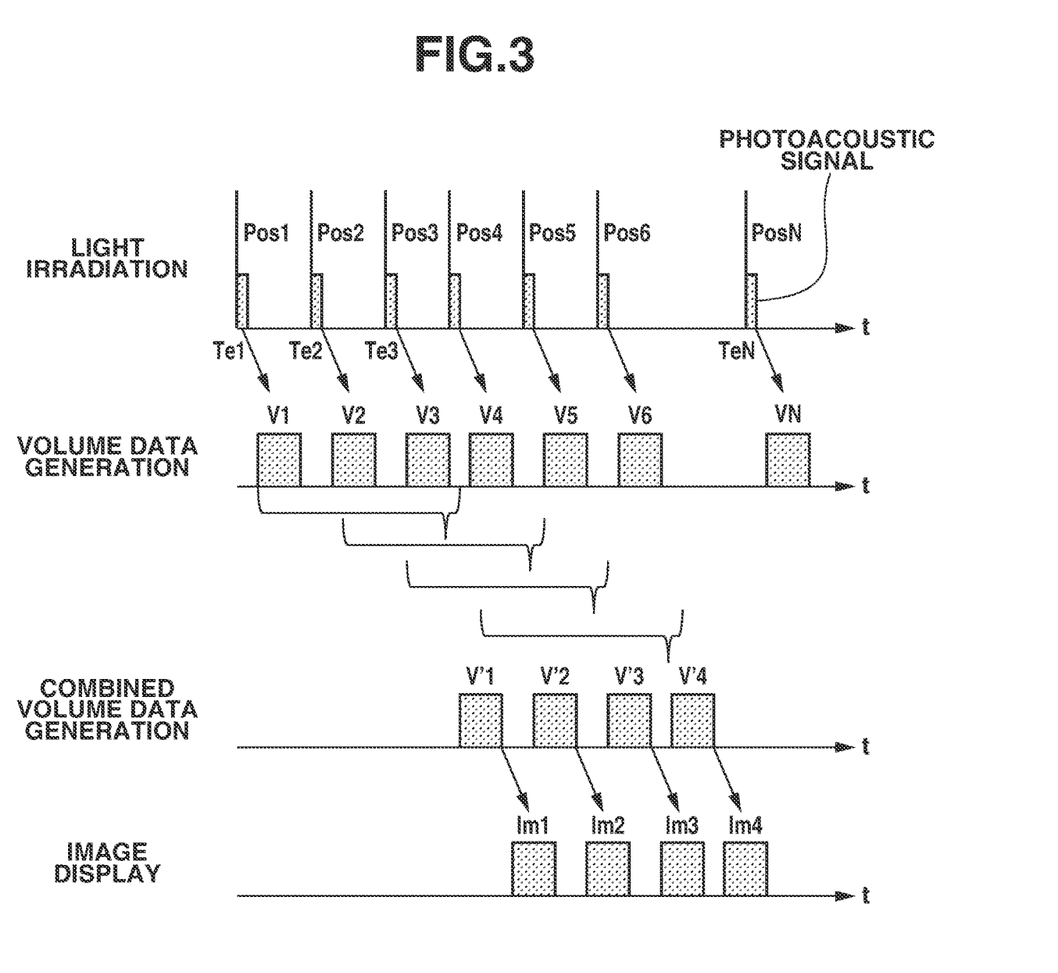
FIG. 3 is a timing chart illustrating operation timings according to the first exemplary embodiment.

FIG. 3 illustrates light irradiation timings and time relations between processing performed by the image generation unit 008 and processing performed by the image processing unit 009. The light irradiation illustrated in FIG. 3 indicates the timings Te1, Te2, Te3, and . . . TeN at which the light irradiation is performed on the subject 013 and the acquisition time of photoacoustic signals acquired in response to respective light irradiations. When photoacoustic signals are acquired by the reception circuit system 006 at respective timings, the image generation unit 008 generates volume data V1, V2, . . . , VN through the image reconstruction based on the acquired photoacoustic signals. The image processing unit 009 further calculates a combined photoacoustic volume V'1 by using three pieces of volume data V1 to V3. According to the present exemplary embodiment, a combined volume data V'n is generated by combining volume data Vn to V(n+2).

Sequentially displaying images corresponding to the thus-acquired combined volume data on the image display unit 010 enables presenting a photoacoustic image updated in real time. The volume data to be combined is volume data which is generated by receiving photoacoustic waves at positions where the high resolution regions mutually overlap. Therefore, images with reduced artifacts can be generated particularly at the positions where overlapping occurs.

This means that combined volume data combines photoacoustic signals acquired during a time period for three light irradiations. If the subject 013 is a living body, the imaging target may move because of a body motion such as breathing. If combined volume data is generated by using photoacoustic signals acquired before and after a body motion, a blur occurs in an image. For this reason, the number of photoacoustic volumes to be used for the combination by the image processing unit 009 can be limited to such an extent that a blur does not largely affect the image. For example, if the cycle of a body motion by breathing is about 0.3 Hz (a cycle of about 3.33 seconds), images with reduced effects of the body motion can be acquired by using photoacoustic signals acquired in a time period shorter than this cycle. If the light irradiation cycle is 10 Hz, limiting the number of volume data to be used for combination to sixteen or less enables acquiring photoacoustic signals to be used for combination within 1.6 seconds, making it possible to perform the combination within a half or less of the body motion cycle. In addition, limiting the number of volume data to be used for combination to eight or less enables acquiring photoacoustic signals to be used for combination within 0.8 seconds, making it possible to acquire combined volume data by using photoacoustic signals acquired at a cycle which is about a quarter of the body motion cycle. The smaller the number of volume data to be used for generation of combined volume data is, images having a higher time resolution can be acquired. Conversely, the larger the number of volume data to be used for generation of combined volume data is, images having a higher S/N ratio can be obtained. The number of volume data may be arbitrarily set via an input unit (not illustrated) by an operator. The convenience for the operator can be improved by displaying the number of volume data to be used for combination. In addition, displaying the acquisition time width of photoacoustic signals used for combination and a cycle (Hz) which can be calculated from the acquisition time width allows the operator to recognize the time resolution of the image to be acquired. This makes it easier for the operator to specify the number of volume data to be used for combination and specify the time resolution.

According to the above-described operations, received data acquired at the position Pos2 is included in images Im1 and Im2 but not included in an image Im3, and a photoacoustic signal acquired at the position Pos3 is included in the images Im1, Im2, and Im3 but not included in an image Im4. This means that the contribution of a photoacoustic signal acquired at a certain position, i.e., volume data using the photoacoustic signal, to the image displayed on the image display unit 010 will decrease with time. As a result, it is possible to reduce artifacts through the combination of volume data and update an image while reducing the contribution of temporally old photoacoustic data to the image.

The above-described operations will be described below in a generalized way. According to the present exemplary embodiment, photoacoustic signals are acquired respectively at N positions at different positions relative to the subject (N is 3 or a larger integer), thus acquiring N pieces of volume data. First combined volume data is generated by combining at least two of the i-th to the (i+m)-th volume data (i+m<N, where i and m are natural numbers). Second combined volume data is generated by combining at least two of the (i+n)-th to the (i+n+m)-th volume data (n is a natural number). Subsequently, the image based on the first combined volume data is updated to the image based on the second combined volume data, and then the first and the second combined image are sequentially displayed.

As illustrated in FIG. 2, photoacoustic signals are received by repetitively moving the probe around a predetermined region (the center of the track 201 in this example), and images acquired by combining a plurality of volume data are sequentially displayed. Then, the operator can view a moving image in a predetermined region. This moving image may be recorded in the image processing unit 009 or a storage device (not illustrated).

When generating combined volume data based on volume data, the combination ratio may be weighted. For example, when generating combined volume data by using volume data V(i) to V(i+m), the ratios of the volume data are set to $\alpha(i)$ to $\alpha(i+m)$, respectively, so that the following condition is satisfied.

$$\alpha(i) \leq \alpha(i+1) \leq \alpha(i+2) \leq \alpha(i+3) \ldots \leq \alpha(i+m)$$

This setting makes it possible to further reduce the contribution of old received data to the combined volume data.

The image display unit 010 may display the time width which has been taken to acquire volume data used for generating the combined image data (for example, the time period since the timing when a photoacoustic signal is acquired at the position Pos1 until the timing when a received signal is acquired at the position Pos3). This allows the operator to grasp the time resolution of the combined image data currently being displayed.

In addition, the image display unit 010 may display the values of the ratios $\alpha(i)$ to $\alpha(i+m)$ of respective volume data at the time of combined volume data generation, and the values can be changed by the operator. This allows the operator to perform adjustment according to the desired time resolution and artifact reduction level.

In an image displayed on the image display unit 010, the image processing unit 009 may emphasize the region corresponding to the high resolution region with respect to other regions.

The present exemplary embodiment is also applicable to a case where a plurality of light sources capable of emitting light with different wavelengths is provided and to a case where a single light source with variable wavelengths is used as the light source 005. For example, when changing the wavelength of the light for irradiating the subject 013 for each pulsed light irradiation, the system control unit 011 may perform the image reconstruction by using photoacoustic signals acquired through the irradiation of light having different wavelengths or by using photoacoustic signals acquired through the irradiations of light with a same single wavelength. In either case, it is desirable that at least two of the high resolution regions at a plurality of timings of photoacoustic signal acquisition overlap. Using only photoacoustic signals acquired through the irradiation of light with the same single wavelength enables acquiring photoacoustic images specific to the wavelength with reduced artifacts. Also when using photoacoustic signals with the same single wavelength of light irradiation, using photoacoustic signals acquired at close timings enables providing photoacoustic images with a high time resolution.

Although, in the present exemplary embodiment, combined volume data is generated based on a plurality of temporally consecutive volume data, it is not always necessary to use all of consecutive volume data. For example, when using a light source capable of emitting light with a high repetition frequency, such as a light emitting diode, using all of a plurality of consecutive volume data will result in a large amount of data. However, the capacity of the storage device and the load on the image processing unit 009 can be reduced by thinning out some volume data when generating combined volume data.

The number of volume data to be used for generation of combined volume data, and the ratio of each volume data when generating combined volume data based on volume data may be stored as preset values, for example, in the storage device included in the system control unit 011. Further, the system control unit 011 may set suitable values from the preset values, for example, according to information such as a department and an observation target portion. The user may refer to patient information such as the input patient identifier (ID). When capturing an image of the same patient again, the user may display a similar setting to the last setting as a candidate, or the system control unit 011 may automatically select a setting.

Figure 4:
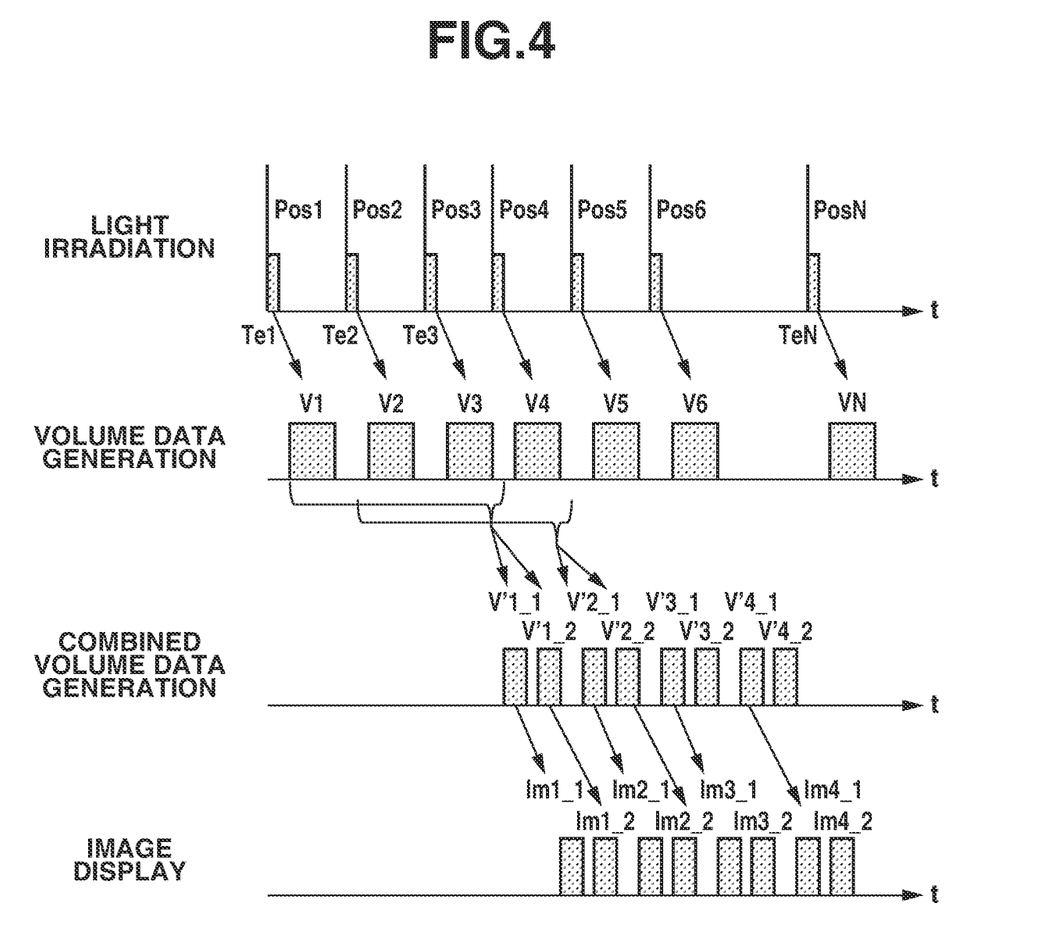
FIG. 4 is a timing chart illustrating operation timings according to a second exemplary embodiment.

A second exemplary embodiment of the present invention will be described below with reference to FIG. 4, centering on differences from the first exemplary embodiment. FIG. 4 illustrates light irradiation timings and time relations between processing performed by the image generation unit 008 and processing performed by the image processing unit 009.

The present exemplary embodiment differs from the first exemplary embodiment in that the image generation unit 008 generates a plurality of combined volume data based on combinations of the same volume data.

As illustrated in FIG. 4, the image generation unit 008 combines three pieces of volume data to generate combined volume data, according to the present exemplary embodiment as well. According to the present exemplary embodiment, the image generation unit 008 generates combined volume data V'1_1 and V'1_2 based on the volume data V1 to V3 by using different weights at the time of volume data combination. More specifically, the weight of the volume data V1 with respect to the volume data V3 in the combined volume data V'1_1 is larger than the weight of the volume data V1 with respect to the volume data V3 in the combined volume data V'1_2. More specifically, an image Im1_1 based on the volume data V'1_1 more strongly reflects information of the volume data V1 which is temporally old volume data than an image Im1_2 based on the volume data V'1_2. Conversely, the image Im1_2 based on the volume data V'1_2 more strongly reflects information of the volume data V3 which is temporally new volume data than the image Im1_1 based on the volume data V'1_1.

According to the present exemplary embodiment, it is possible not only to provide a moving image with reduced artifacts but also to generate combined volume data at a higher frequency than the repetition frequency for acquiring photoacoustic signals, thus enabling the image to be updated at high frame rates.

Figure 5:
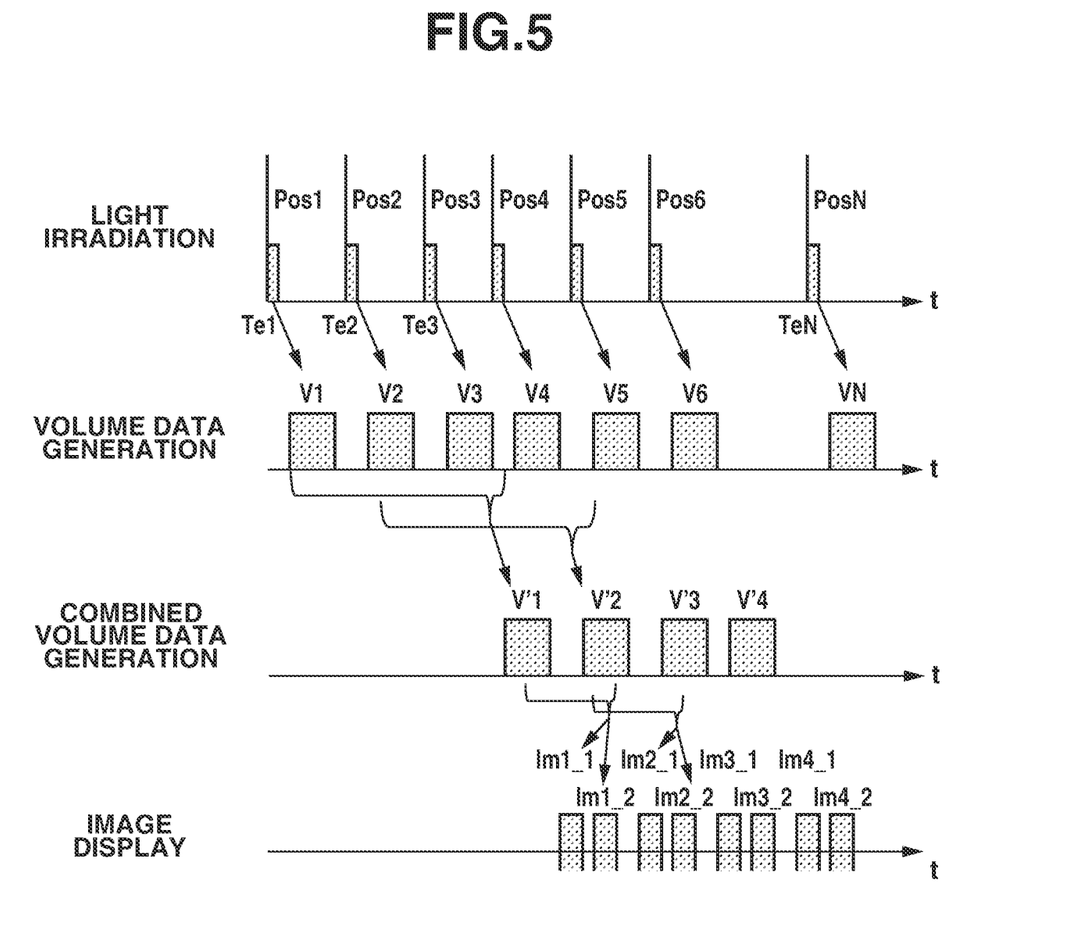
FIG. 5 is a timing chart illustrating operation timings according to a third exemplary embodiment.

A third exemplary embodiment of the present invention will be described below with reference to FIG. 5. The present exemplary embodiment will be described below centering on differences from the first exemplary embodiment. FIG. 5 illustrates light irradiation timings and time relations between processing performed by the image generation unit 008 and processing performed by the image processing unit 009.

The present exemplary embodiment differs from the first exemplary embodiment in that a plurality of combined volume data is combined to generate combined image data.

In operations illustrated in FIG. 5, the images Im1_1 and Im1_2 are generated based on the combined volume data V'1 and V'2. In this case, the contribution of the combined volume data V'1 to the image Im1_1 is larger than the contribution of the combined volume data V'2 to the image Im1_2.

According to the present exemplary embodiment, it is possible not only to provide a moving image with reduced artifacts but also to output combined image data at a higher frequency than the frequency for generating combined volume data, thus enabling the image to be updated at high frame rates.

Figure 6:
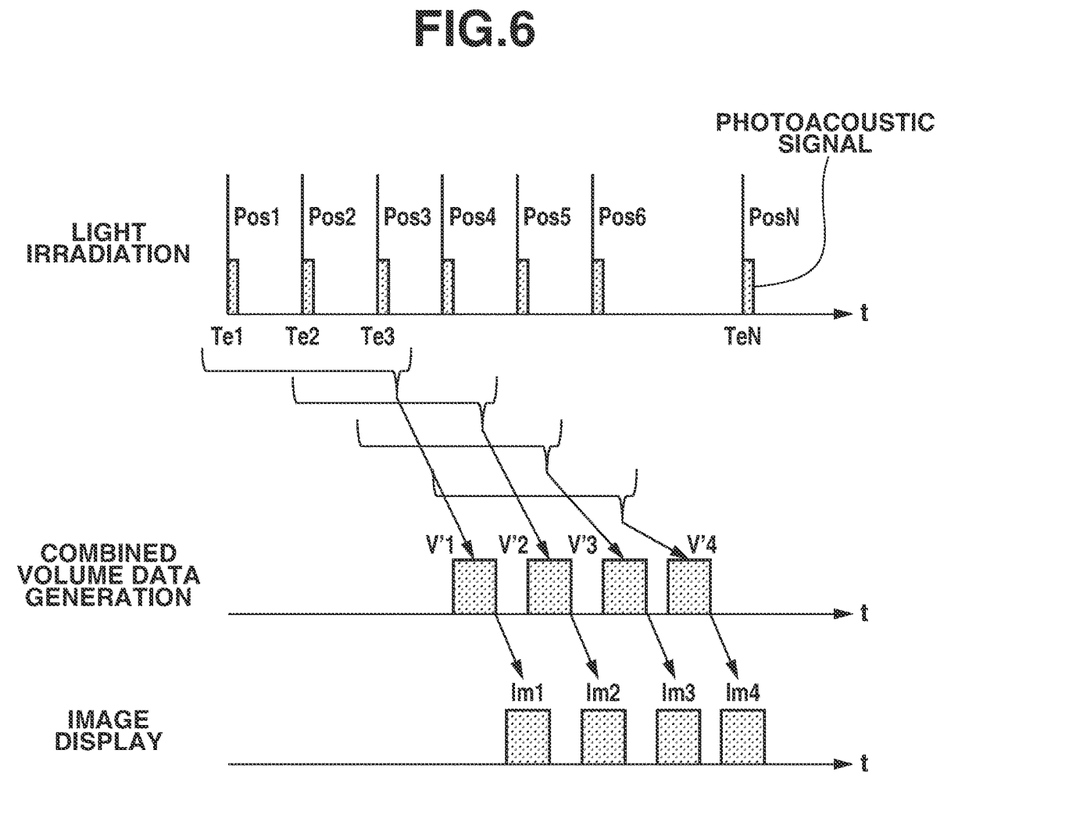
FIG. 6 is a timing chart illustrating operation timings according to a fourth exemplary embodiment.

A fourth exemplary embodiment of the present invention will be described below with reference to FIG. 6. The present exemplary embodiment will be described below centering on differences from the first exemplary embodiment. FIG. 6 illustrates light irradiation timings and time relations between processing performed by the image generation unit 008 and processing performed by the image processing unit 009.

The present exemplary embodiment differs from the first exemplary embodiment in that combined volume data is generated based on photoacoustic signal groups acquired through a plurality of light irradiations without individually generating volume data based on a photoacoustic signal acquired through each light irradiation.

In the example illustrated in FIG. 6, the image generation unit 008 generates one piece of combined volume data based on photoacoustic signals acquired through three light irradiations. The image generation unit 008 reads photoacoustic signals acquired at the timings Te1, Te2, and Te3 from the storage device and generates the combined volume data V'1. Subsequently, the image processing unit 009 performs predetermined image processing on the combined volume data V'1, and the system control unit 011 controls the image display unit 010 to display the image Im1.

According to the present exemplary embodiment, it is possible to provide a moving image with reduced artifacts.

Although, in the present exemplary embodiment, the image generation unit 008 generates combined volume data based on a plurality of temporally consecutive photoacoustic signals, it is not always necessary to use all of consecutive photoacoustic signals. For example, when using a light source capable of emitting light with a high repetition frequency, such as a light emitting diode, using all of a plurality of consecutive photoacoustic signals will results in a large amount of data. Therefore, the capacity of the storage device and the load on the image processing unit 009 can be reduced by thinning out some photoacoustic signals at the time of combined volume data generation.

The above-described exemplary embodiments are to be considered as illustrative, and can be suitably modified or combined without departing from the technical idea of the present invention.

According to the present invention, it is possible to acquire a moving image by consecutively receiving acoustic waves from an observation target subject region.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-001409, filed Jan. 6, 2017, which is hereby incorporated by reference herein in its entirety.

What is claimed is:

1. A subject information processing apparatus comprising:
a light irradiation unit configured to irradiate a subject with light;
a probe configured to detect acoustic waves generated at the subject in response to light irradiation by the light irradiation unit;
a signal processing unit configured to generate image data of a subject based on electrical signals output from the probe detecting acoustic waves propagated from the subject; and
a display control unit configured to control a display unit to display an image based on the image data,
wherein the signal processing unit combines at least two of i-th image data to (i+m)-th image data (i+m<N, where i and m are natural numbers) out of N pieces of image data based on electrical signals acquired with a first inclined weighting manner so that weights in association with the i-th image data to the (i+m)-th image data increase in this order, when the probe detects the acoustic waves respectively at N positions (N is 3 or a larger integer) at different relative positions to the subject to generate first combined image data,
wherein the signal processing unit combines at least two of (i+n)-th image data to (i+n+m)-th image data (n is a natural number) with a second inclined weighting manner so that weights in association with the (i+n)-th image data to the (i+n+m)-th image data increase in this order, to generate second combined image data, and
wherein the display control unit controls the display unit to display an image based on the first combined image data, and further updates the image displayed on the display unit to an image based on the second combined image data.

2. The subject information processing apparatus according to claim 1, wherein the signal processing unit sets a contribution of p-th image data (p<m, where p is a natural number) to the second combined image data to be lower than a contribution of the p-th image data to the first combined image data.

3. The subject information processing apparatus according to claim 2, wherein the signal processing unit sets the contribution of the p-th image data to the second combined image data to zero.

4. The subject information processing apparatus according to claim 1, wherein the display control unit controls the display unit to further display information about a time resolution when updating the image based on the first combined image data to the image based on the second combined image data.

5. The subject information processing apparatus according to claim 1, further comprising:
a moving unit configured to change the relative position of the probe to the subject.

6. The subject information processing apparatus according to claim 1,
wherein the probe includes
a plurality of acoustic wave detection elements configured to respectively output the electrical signals in response to detection of the acoustic waves; and
a supporting member configured to support a plurality of the acoustic wave detection elements so that directional axes of the plurality of the acoustic wave detection elements are concentrated.

7. The subject information processing apparatus according to claim 6, further comprising:
a moving unit configured to change the relative position of the probe to the subject,
wherein, for two consecutive light irradiations, the moving unit moves the probe so that high resolution regions overlap, wherein each of the high resolution regions is defined by concentrated directional axes of a plurality of the acoustic wave detection elements.

8. The subject information processing apparatus according to claim 7, wherein, a region corresponding to at least one of the high resolution regions in an image to be displayed on the display unit is emphasized with respect to a region corresponding to a region other than the high resolution regions.

9. The subject information processing apparatus according to claim 7, wherein the display control unit controls the display unit to display an image corresponding only to the region corresponding to one of the high resolution regions.

10. The subject information processing apparatus according to claim 1, further comprising a storage unit configured to store the electrical signals and information about positions of the probe when acoustic waves as a basis of the electrical signals are received.

11. The subject information processing apparatus according to claim 1, wherein the light irradiation unit irradiates the subject with the light at relative positions of the N positions of the probe to the subject, and the light irradiated at the relative positions of the N positions irradiates mutually overlapped regions.

12. An image display method for displaying an image of a subject based on acoustic waves propagated from the subject, the method comprising:
   irradiating the subject with light;
   detecting acoustic waves generated at the subject in response to light irradiation by the light irradiating and generating electrical signals based on the detected acoustic waves;
   combining at least two of i-th image data to (i+m)-th image data (i+m<N, where i and m are natural numbers) out of N pieces of image data based on electrical signals acquired with a first inclined weighting manner so that weights in association with the i-th image data to the (i+m)-th image data increase in this order, when a probe detects the acoustic waves respectively at N positions (N is 3 or a larger integer) at different relative positions to the subject to generate first combined image data;
   combining at least two of (i+n)-th image data to (i+n+m)-th image data (n is a natural number) with a second inclined weighting manner so that weights in association with the (i+n)-th image data to the (i+n+m)-th image data increase in this order, to generate second combined image data;
   displaying, on a display unit, an image based on the first combined image data; and
   updating the image displayed on the display unit to an image based on the second combined image data.

13. The image display method according to claim 12, wherein a contribution of p-th image data (p<m, where p is natural number) to the second combined image data is lower than a contribution of the p-th image data to the first combined image data.

14. The image display method according to claim 13, wherein the contribution of the p-th image data to the second combined image data is zero.

15. The image display method according to claim 12, wherein the display unit further displays information about a time resolution when updating the image based on the first combined image data to the image based on the second combined image data.

16. A subject information processing apparatus comprising:
   a light irradiation unit configured to irradiate a subject with light;
   a probe configured to detect acoustic waves generated at the subject in response to light irradiation by the light irradiation unit;
   a signal processing unit configured to generate image data of a subject based on electrical signals output from the probe detecting acoustic waves propagated from the subject; and
   a display control unit configured to control a display unit to display an image based on the image data,
   wherein the signal processing unit uses at least two of an i-th to an (i+m)-th electrical signal (i+m<N, where i and m are natural numbers) out of N electrical signal groups acquired with a first inclined weighting manner so that weights in association with the i-th electrical signal to the (i+m)-th electrical signal increase in this order, when the probe detects the acoustic waves respectively at N positions (N is 3 or a larger integer) at different relative positions to the subject to generate first combined image data,
   wherein the signal processing unit uses at least two of an (i+n)-th to an (i+n+m)-th electrical signal (n is a natural number) with a second inclined weighting manner so that weights in association with the (i+n)-th electrical signal to the (i+n+m)-th electrical signal increase in this order, to generate second combined image data, and
   wherein the display control unit controls the display unit to display an image based on the first combined image data, and further updates the image displayed on the display unit to an image based on the second combined image data.

* * * * *